United States Patent
Jarsch et al.

(10) Patent No.: US 8,623,666 B2
(45) Date of Patent: Jan. 7, 2014

(54) METHOD FOR DETECTING ERYTHROPOIETIN (EPO) RECEPTOR USING ANTI-HUMAN EPO RECEPTOR ANTIBODIES

(75) Inventors: Michael Jarsch, Bad Heilbrunn (DE); Olaf Mundigl, Weilheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/517,826

(22) Filed: Jun. 14, 2012

(65) Prior Publication Data

US 2012/0321633 A1 Dec. 20, 2012

(30) Foreign Application Priority Data

Jun. 15, 2011 (EP) ..................................... 11170020

(51) Int. Cl.
| | | |
|---|---|---|
| *G01N 33/567* | (2006.01) | |
| *C12N 5/07* | (2010.01) | |
| *C12N 5/16* | (2006.01) | |
| *G01N 33/566* | (2006.01) | |

(52) U.S. Cl.
USPC ........... 436/503; 435/7.21; 435/331; 436/501

(58) Field of Classification Search
None
See application file for complete search history.

(56) References Cited

U.S. PATENT DOCUMENTS

| | | |
|---|---|---|
| 6,153,190 A | 11/2000 | Young et al. |
| 6,998,124 B1 | 2/2006 | Erickson-Miller et al. |
| 7,053,184 B2 | 5/2006 | Lee |
| 7,081,523 B2 | 7/2006 | Elliott |
| 2002/0031806 A1 | 3/2002 | Lee |
| 2003/0215444 A1 | 11/2003 | Elliott |
| 2004/0058393 A1 | 3/2004 | Fukishima et al. |
| 2004/0071694 A1 | 4/2004 | DeVries et al. |
| 2004/0175379 A1 | 9/2004 | DeVries et al. |
| 2005/0227289 A1 | 10/2005 | Reilly et al. |
| 2005/0244409 A1 | 11/2005 | Erickson-Miller et al. |
| 2006/0018902 A1 | 1/2006 | Reilly et al. |

FOREIGN PATENT DOCUMENTS

| | | |
|---|---|---|
| EP | 0 773 962 B1 | 5/1997 |
| EP | 0 776 370 B1 | 6/1997 |
| EP | 1 146 056 A1 | 10/2001 |
| EP | 1 327 681 A1 | 7/2003 |
| WO | 95/05469 A1 | 2/1995 |
| WO | 96/03438 A1 | 2/1996 |
| WO | 00/61637 A1 | 10/2000 |
| WO | 2004/035603 A2 | 4/2004 |
| WO | 2005/100403 A2 | 10/2005 |
| WO | 2010/022924 A1 | 3/2010 |
| WO | 2010/054007 A1 | 5/2010 |
| WO | 2010/081679 A2 | 7/2010 |
| WO | 2010/136192 A1 | 12/2010 |

OTHER PUBLICATIONS

Mayeux et al., "Structure of the Murine Erythropoietin Receptor Complex" J Biol Chem 266(34):23380-23385 (Dec. 1991).
Laugsch et al., "Lack of Functional Erythropoietin Receptors of Cancer Cell Lines" Int J Cancer 122:1005-1011 (2008).
Kirkeby et al., "Functional and Immunochemical Characterisation of Different Antibodies Against the Erythropoietin Receptor" J Neurosci Meth 164:50-58 (2007).
Elliott et al., "Anti-Epo Receptor Antibodies do not Predict Epo Receptor Expression" Blood 107:1892-1895 (2006).
Winkelmann et al., "The Gene for the Human Erythropoietin Receptor: Analysis of the Coding Sequence and Assignment to Chromosome 19p" Blood 76:24-30 (1990).
PCT ISR and Written Opinion for PCT/EP2012/061288.
Jones et al., "Human Erythropoietin Receptor: Cloning, Expression, and Biologic Characterization" Blood 76:31-35 (1990).
Miura et al., "Dimer- and Oligomerization of the Erythropoietin Receptor by Disulfide Bond Formation and Significance of the Region near the WSXWS Motif in Intracellular Transport" Arch Biochem Biophys 306(1):200-208 (Oct. 1993).
European Search Report for EP 11170020.
Elliott et al., "Identification of a sensitive anti-erythropoietin receptor monoclonal antibody allows detection of low levels of EpoR in cells" J Immunol Methods 352:126-39 (Jan. 2010).
Jelkmann et al., "Th Erythropoietin Receptor in Normal and Cancer Tissues" Crit Rev Oncol Hemat 67:39-61 (2008).
D'Andrea et al., "Anti-Erythropoietin Receptor (EPO-R) Monoclonal Antibodies Inhibit Erythropoietin Binding and Neutralize Bioactivity" Blood 82(1):46-52 (Jul. 1993).
Brown et al., "Erythropoietin receptor expression in non-small cell lung carcinoma: a question of antibody specificity" Stem Cells 25:718-22 (2007).
Wu et al., "Functional interaction of erythropoietin and stem cell factor receptors is essential for erythroid colony formation" Proc. Natl. Acad. Sci. 94:1806-1810 (Mar. 1997).
Westphal et al., "Detection and Quantification of the Soluble Form of the Human Erythropoietin Receptor (sEpoR) in the Growth Medium of Tumor Cell Lines and in the Plasma of Blood Samples" Clin Exp Med 2:45-52 (2002).
Jelkmann et al., "Problems in Identifying Functional Erythropoietin Receptors in Cancer Tissue" J Clin Oncol 25(12):1627-1628 (Apr. 2007).
Anonymous, "Anti human EPOR antibody C-20:SC-695 datasheet, Santa Cruz Biotechnology Inc. [Online]" (2000).
Anonymous, "Anti mouse EPOR antibody M-20: SC-697 datasheet, Santa Cruz Biotechnology Inc. [Online]" (2000).
Huston, J. et al., "Protein engineering of single-chain Fv analogs and fusion proteins" Methods in Enzymology 203:46-88 (1991).

*Primary Examiner* — Robert Landsman
(74) *Attorney, Agent, or Firm* — Jennifer K. Holmes

(57) ABSTRACT

Herein is reported an antibody that specifically binds to human EPO receptor, wherein the antibody binds to EPO receptor fragment LPGPGGSVDIV (SEQ ID NO: 01) but that does not specifically bind to a protein obtainable from human endothelial cells that has a molecular weight of about 66 kD.

10 Claims, 4 Drawing Sheets

```
SEQUENCE LISTING

<160> NUMBER OF SEQ ID NOS: 3

<210> SEQ ID NO 1
<211> LENGTH: 11
<212> TYPE: PRT
<213> ORGANISM: Homo sapiens

<400> SEQUENCE: 1

Leu Pro Gly Pro Gly Gly Ser Val Asp Ile Val
1               5                   10

<210> SEQ ID NO 2
<211> LENGTH: 25
<212> TYPE: PRT
<213> ORGANISM: Homo sapiens

<400> SEQUENCE: 2

Leu Asp Lys Trp Leu Leu Pro Arg Asn Pro Pro Ser Glu Asp Leu Pro
1               5                   10                  15

Gly Pro Gly Gly Ser Val Asp Ile Val
            20                  25

<210> SEQ ID NO 3
<211> LENGTH: 508
<212> TYPE: PRT
<213> ORGANISM: Homo sapiens

<400> SEQUENCE: 3

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160
```

-continued

```
His Val Val Leu Arg Trp Leu Pro Pro Pro Glu Thr Pro Met Thr Ser
                    165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
        210                 215                 220

Ala Glu Pro Ser Phe Gly Gly Phe Trp Ser Ala Trp Ser Glu Pro Val
225                     230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
                260                 265                 270

Ser His Arg Arg Ala Leu Lys Gln Lys Ile Trp Pro Gly Ile Pro Ser
            275                 280                 285

Pro Glu Ser Glu Phe Glu Gly Leu Phe Thr Thr His Lys Gly Asn Phe
        290                 295                 300

Gln Leu Trp Leu Tyr Gln Asn Asp Gly Cys Leu Trp Trp Ser Pro Cys
305                     310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
                340                 345                 350

Gly Pro Leu Leu Glu Pro Val Gly Ser Glu His Ala Gln Asp Thr Tyr
            355                 360                 365

Leu Val Leu Asp Lys Trp Leu Leu Pro Arg Asn Pro Pro Ser Glu Asp
        370                 375                 380

Leu Pro Gly Pro Gly Gly Ser Val Asp Ile Val Ala Met Asp Glu Gly
385                     390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
                420                 425                 430

Ser Gln Leu Leu Arg Pro Trp Thr Leu Cys Pro Glu Leu Pro Pro Thr
            435                 440                 445

Pro Pro His Leu Lys Tyr Leu Tyr Leu Val Val Ser Asp Ser Gly Ile
        450                 455                 460

Ser Thr Asp Tyr Ser Ser Gly Asp Ser Gln Gly Ala Gln Gly Gly Leu
465                     470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
                500                 505
```

METHOD FOR DETECTING ERYTHROPOIETIN (EPO) RECEPTOR USING ANTI-HUMAN EPO RECEPTOR ANTIBODIES

RELATED APPLICATIONS

This application claims the benefit of EP Application No. 11170020.9, filed Jun. 15, 2011. All the teachings of the above-referenced application are incorporated herein by reference.

SEQUENCE LISTING

The instant application contains a Sequence Listing which has been submitted in ASCII format via EFS-Web and is hereby incorporated by reference in its entirety. Said ASCII copy, created on May 25, 2012, is named P4701SeqList.txt and is 5,118 bytes in size.

FIELD OF THE INVENTION

The present invention relates to anti-human EPO receptor antibodies and methods of using the same.

BACKGROUND

Human erythropoietin (EPO) is a 166-aa glycoprotein which is involved in the proliferation and differentiation of erythroid progenitor cells. These cellular responses are mediated by the human EPO receptor (EPO receptor, EPOR), a 508-aa glycoprotein. EPO receptor is a protein of 508 amino acid length (Swiss Prot P19235) containing a single transmembrane domain and has been classified as a member of the growth hormone subfamily of class I cytokine receptors. EPO receptor is described, e.g., in Winkelmann, J. C., et al., Blood 76 (1990) 24-30, and Jones, S. S., et al., Blood 76 (1990) 31-35).

Antibodies against EPO receptor are known from, e.g., D'Andrea, A. D., Blood 82 (1993) 46-52; Elliott, S., Blood 107 (2006) 1892-1895; Kirkeby, A., J. Neurosci. Methods 164 (2007) 50-58; Miura, O., Arch. Biochem. 306 (1993) 200-208; Mayeux, P., et al., J. Biol. Chem. 266 (1991) 23380-23385; Westphal. G., et al., Clin. Exp. Med. 2 (2002) 45-52; Elliott, S., et al., J. Immunol. Meth. 352 (2010) 126-139, and EP 1 146 056, EP 1 327 681, EP 0 773 962, EP 0 776 370, US 2002/0031806, US 2003/0215444, US 2004/0058393, US 2004/0071694, US 2004/0175379, US 2005/0227289, US 2005/0244409, US 2006/0018902, U.S. Pat. Nos. 6,153,190, 6,998,124, 7,053,184, 7,081,523, WO 1995/005469, WO 1996/003438, WO 2000/061637, WO 2004/035603, WO 2005/100403, and WO 2010/022924. However, studies investigating the expression and localization of EPO receptor in tissue samples produce divergent and often artifactual results because lack of specificity of known antibodies against EPO receptor (see Jelkmann, W., et al., Crit. Rev. Onc. Hematol. 67 (2008) 39-61; Elliott, S., et al., Blood 107 (2006) 1892-1895; Jelkmann, W. and Laugsch, M., J. Clin. Oncol. 25 (2007) 1627-1628; Kirkeby, A., et al., J. Neurosci. Methods 164 (2007) 50-58; Laugsch, M. et al., Int. J. Cancer 122 (2008) 1005-1011), or it was reported that studies employed antibodies with questionable specificity and the significance of the observations are controversial (Elliott, S. above).

SUMMARY

It has been found that antibodies as reported herein bind specifically to human EPO receptor without being cross-reactive to proteins of similar size present on/in endothelial cells allowing for unambiguous detection results.

One aspect as reported herein is a method for detecting in vitro human EPO receptor comprising the step of determining in vitro the presence of human EPO receptor in a sample by incubating the sample with an EPO receptor antibody that specifically binds to human EPO receptor fragment LPG-PGGSVDIV (SEQ ID NO: 01) and thereby detecting in vitro human EPO receptor, wherein the EPO receptor antibody that specifically binds to EPO receptor fragment LPGPGGS-VDIV (SEQ ID NO: 01) does not specifically bind to a protein obtainable from human endothelial cells that has a molecular weight of about 58 kD to about 70 kD.

In one embodiment the method is characterized in that the antibody does not specifically bind to a protein obtainable from human endothelial cells that has a molecular weight of about 66 kD.

In one embodiment the method is characterized in that the antibody binds to the protein obtainable from human endothelial cells with an affinity of $10^{-3}$M or higher.

In one embodiment the method is characterized in that the antibody is a polyclonal antibody or a monoclonal antibody.

In one embodiment the method is characterized in that the antibody is a human, humanized, or chimeric antibody.

In one embodiment the method is characterized in that the antibody is an antibody fragment that binds human EPO receptor.

An aspect as reported herein is an antibody that specifically binds to human EPO receptor, characterized in that the antibody binds to human EPO receptor fragment LPGPGGS-VDIV (SEQ ID NO: 01) and does not specifically bind to a protein obtainable from human endothelial cells that has a molecular weight of about 58 kD to about 70 kD.

In one embodiment the antibody is characterized in that it does not specifically bind to a protein obtainable from human endothelial cells that has a molecular weight of about 66 kD.

In one embodiment the antibody is characterized in that it binds to the protein obtainable from human endothelial cells with an affinity of $10^{-3}$M or higher.

In one embodiment the antibody is characterized in that it is a polyclonal antibody or a monoclonal antibody.

In one embodiment the antibody is characterized in that it is a human, humanized, or chimeric antibody.

In one embodiment the antibody is characterized in that it is an antibody fragment that binds human EPO receptor.

An aspect as reported herein is an antibody that specifically binds to human EPO receptor that can be used in a method as reported herein.

An aspect as reported herein is an antibody that specifically binds to human EPO receptor for use in a method as reported herein.

In one embodiment the antibody is characterized in that the antibody binds to EPO receptor fragment LPGPGGSVDIV (SEQ ID NO: 01) and does not specifically bind to a protein obtainable from human endothelial cells that has a molecular weight of about 58 kD to about 70 kD.

In one embodiment the antibody is characterized in that it does not specifically bind to a protein obtainable from human endothelial cells that has a molecular weight of about 66 kD.

In one embodiment the antibody is characterized in that it binds to the protein obtainable from human endothelial cells with an affinity of $10^{-3}$M or higher.

In one embodiment the antibody is characterized in that it is a polyclonal antibody or a monoclonal antibody.

In one embodiment the antibody is characterized in that it is a human, humanized, or chimeric antibody.

In one embodiment the antibody is characterized in that it is an antibody fragment that binds human EPO receptor.

An aspect as reported herein is the use of an antibody that specifically binds to human EPO receptor, characterized in that the antibody binds to EPO receptor fragment LPGPGGSVDIV (SEQ ID NO: 01) and does not specifically bind to a protein obtainable from human endothelial cells that has a molecular weight of about 58 kD to about 70 kD for detecting human EPO receptor.

In one embodiment the use is characterized in that the antibody does not specifically bind to a protein obtainable from human endothelial cells that has a molecular weight of about 66 kD.

In one embodiment the use is characterized in that the antibody binds to the protein obtainable from human endothelial cells with an affinity of $10^{-3}$ M or higher.

In one embodiment the use is characterized in that the antibody is a polyclonal antibody or a monoclonal antibody.

In one embodiment the use is characterized in that the antibody is a human, humanized, or chimeric antibody.

In one embodiment the use is characterized in that the antibody is an antibody fragment that binds human EPO receptor.

An aspect as reported herein is a method for predicting or determining the responsiveness of a patient towards a medicament for increasing the number of red blood cells comprising determining in vitro the presence of human EPO receptor on cancer cells of the patient by incubating in vitro a sample of the patient with the EPO receptor antibody as reported herein and determining in vitro the binding of the antibody to the sample, whereby the presence of human EPO receptor on the cancer cells of the patient is indicative for the responsiveness of the patient towards a medicament for increasing the number of red blood cells.

In one embodiment the method is characterized in that the antibody does not specifically bind to a protein obtainable from human endothelial cells that has a molecular weight of about 58 kD to about 70 kD, in one embodiment of about 66 kD.

In one embodiment the method is characterized in that the antibody binds to the protein obtainable from human endothelial cells with an affinity of $10^{-3}$ M or higher.

In one embodiment the method is characterized in that the antibody is a polyclonal antibody or a monoclonal antibody.

In one embodiment the method is characterized in that the antibody is a human, humanized, or chimeric antibody.

In one embodiment the method is characterized in that the antibody is an antibody fragment that binds human EPO receptor.

Herein are reported antibodies that specifically bind to the human EPO receptor fragment that has the amino acid sequence LPGPGGSVDIV (SEQ ID NO: 01) and that do not bind to human endothelial cells. It has been found that such antibodies can be obtained by immunizing an experimental animal with the EPO receptor fragment that has the amino acid sequence LDKWLLPRNPPSEDLPGPGGSVDIV (SEQ ID NO: 02) and thereafter cross-adsorbing, i.e. selecting, the antibodies obtained from the experimental animal to the EPO receptor fragment with the amino acid sequence LPGPGGSVDIV (SEQ ID NO: 01).

An aspect as reported herein is a method for producing an antibody that specifically binds to human EPO receptor comprising the following steps:

immunizing an animal with a polypeptide comprising the EPO receptor fragment LDKWLLPRNPPSEDLPGPGGSVDIV (SEQ ID NO: 02), and selecting an antibody that binds to the EPO receptor fragment LPGPGGSVDIV (SEQ ID NO: 01) and thereby producing an antibody that specifically binds to human EPO receptor.

In one embodiment the selecting is by cross-adsorbing the antibodies obtained from the immunized animal to immobilized EPO receptor fragment of SEQ ID NO: 01.

In one embodiment the method is characterized in that the antibody does not specifically bind to a protein obtainable from human endothelial cells that has a molecular weight of about 58 kD to about 70 kD, in one embodiment of about 66 kD.

In one embodiment the method is characterized in that the antibody binds to the protein obtainable from human endothelial cells with an affinity of $10^{-3}$ M or higher.

In one embodiment the method is characterized in that the antibody is a polyclonal antibody or a monoclonal antibody.

In one embodiment the method is characterized in that the antibody is a human, humanized, or chimeric antibody.

In one embodiment the method is characterized in that the antibody is an antibody fragment that binds human EPO receptor.

An aspect as reported herein is an antibody that specifically binds to human EPO receptor, wherein the antibody binds to EPO receptor fragment LPGPGGSVDIV (SEQ ID NO: 01).

In one embodiment the antibody has an affinity of $10^{-7}$ M or less to the human EPO receptor. In one embodiment the antibody has an affinity to the human EPO receptor of $10^{-8}$ M or less. In one embodiment the antibody has an affinity to the human EPO receptor of $5 \times 10^{-9}$ M or less. In one embodiment the antibody has an affinity to the human EPO receptor of $2 \times 10^{-9}$ M or less. In one embodiment the antibody has an affinity to the human EPO receptor of about $1.8 \times 10^{-9}$ M. In one embodiment the antibody has an affinity to the human EPO receptor of at least $5 \times 10^{-10}$ M. In one embodiment the antibody has an affinity to the human EPO receptor of at least about $6.3 \times 10^{-10}$ M.

In one embodiment of all aspects the antibody is a polyclonal antibody or a monoclonal antibody.

In one embodiment of all aspects the antibody is a mouse, or rat, or rabbit, or hamster, or sheep, or goat, or chicken, or monkey, or pig, or human, or humanized antibody. In one embodiment the antibody is a human antibody, a humanized antibody, or a chimeric antibody.

In one embodiment the antibody is an antibody fragment that specifically binds the human EPO receptor.

An aspect as reported herein is an isolated nucleic acid encoding the antibody as reported herein.

An aspect as reported herein is a host cell comprising the nucleic acid encoding the antibody as reported herein.

An aspect as reported herein is a method of producing an antibody as reported herein comprising culturing the host cell as reported herein so that the antibody is produced.

In one embodiment the method comprises the step of recovering the antibody from the host cell or the cultivation medium.

In one embodiment the host cell is a prokaryotic cell or a eukaryotic cell. In one embodiment the cell is a CHO cell, or a HEK cell, or a BHK cell, or a Sp2/0 cell, or a NS0 cell.

In one embodiment the cell is an *E. coli* cell or a *Bacillus* cell.

An aspect as reported herein is a method for producing an antibody that specifically binds to the human EPO receptor comprising the following steps:

immunizing an animal with a polypeptide comprising the EPO receptor fragment LDKWLLPRNPPSEDLPGPGGSVDIV (SEQ ID NO: 02), and selecting an antibody that binds to the EPO receptor fragment LPGPGGSVDIV (SEQ ID NO: 1), and thereby producing an antibody that specifically binds to the human EPO receptor.

In one embodiment the method comprises one or more of the following additional steps:

cultivating a cell comprising a nucleic acid encoding the antibody that has been selected, and/or recovering the antibody from the cell or the cultivation medium.

An aspect as reported herein is an immunoconjugate comprising the antibody as reported herein and a detectable label or a cytotoxic agent.

An aspect as reported herein is a pharmaceutical formulation comprising the antibody as reported herein and optionally a pharmaceutically acceptable carrier.

An aspect as reported herein is a diagnostic formulation comprising the antibody as reported herein conjugated to a detectable label.

An aspect as reported herein is the antibody as reported herein for use as a medicament.

An aspect as reported herein is the antibody as reported herein for use in treating anemia.

An aspect as reported herein is the antibody as reported herein for use in changing the number of red blood cells in a patient.

An aspect as reported herein is the use of the antibody as reported herein in the manufacture of a medicament.

In one embodiment the medicament is for the treatment of anemia.

In one embodiment the medicament is for changing the number of red blood cells in a patient.

An aspect as reported herein is a method of treating an individual having anemia comprising administering to the individual an effective amount of the antibody as reported herein for changing/increasing the number of red blood cells in the individual.

An aspect as reported herein is a method of changing the number of red blood cells in an individual comprising administering to the individual an effective amount of the antibody as reported herein to change the number of red blood cells in the individual.

An aspect as reported herein is a diagnostic kit comprising an antibody as reported herein.

An aspect as reported herein is a method for the manufacture of a diagnostic kit comprising an antibody as reported herein.

An aspect as reported herein is the use of an antibody as reported herein for the determination or analysis of the human EPO receptor in a human tissue sample.

In one embodiment of all aspects the sample is a lysate of human tissue or human cells.

In one embodiment of all aspects the sample is a section of tissue, or a section of a fresh tissue, or frozen tissue, or a section of frozen tissue, or formalin-fixed paraffin embedded tissue, or a section of formalin-fixed paraffin embedded tissue.

In one embodiment of all aspects the analysis is performed by immunochemistry, immunofluorescence, or immunohistochemistry. In one embodiment the analysis is performed by Western Blot, or by FACS, or by in-vivo imaging using NIRF or PET.

In one embodiment of all aspects the determination is by incubating the tissue sample with the antibody as reported herein and detecting the binding of the antibody to the tissue sample.

An aspect as reported herein is a method for predicting or determining the responsiveness of a patient towards a medicament for increasing the number of red blood cells comprising determining in vitro the presence of human EPO receptor on cancer cells of the patient, and associating the presence of the human EPO receptor on the cancer cells of the patient with the responsiveness of the patient towards a medicament for increasing the number of red blood cells.

An aspect as reported herein is a method for determining the dose of a medicament for increasing the number of red blood cells for treating a cancer patient, the method comprising:

determining in vitro the presence of human EPO receptor on cancer cells of the patient, and when determining the presence of human EPO receptor deciding to administer no or a lower dose of a medicament that increases the number of red blood cells, and when determining the absence of human EPO receptor deciding to administer a dose of a medicament that increases the number of red blood cells.

An aspect as reported herein is a method for predicting or determining the responsiveness of a patient towards a medicament for increasing the number of red blood cells comprising determining in vitro the density of human EPO receptor on cancer cells of the patient, associating the density of human EPO receptors on the cancer cells of the patient with the responsiveness of the patient towards a medicament for increasing the number of red blood cells.

An aspect as reported herein is a method for determining the dose of a medicament for increasing the number of red blood cells for treating a cancer patient, the method comprising:

determining in vitro the presence of human EPO receptor on cancer cells of the patient, and in the presence of the human EPO receptor deciding to administer no or a lower dose of a medicament that increases the number of red blood cells, and in the absence of the human EPO receptor deciding to administer a normal dose of a medicament that increases the number of red blood cells.

In one embodiment of all aspects the determining of the presence of human EPO receptor on cancer cells or the determining of the density of human EPO receptor on the cancer cells is by incubating in vitro a tissue sample of the patient with an EPO receptor antibody as reported herein and determining in vitro the binding of the antibody to the sample.

In one embodiment the medicament that increases the number of red blood cells is erythropoietin.

BRIEF DESCRIPTION OF THE SEQUENCES

Figure 1:
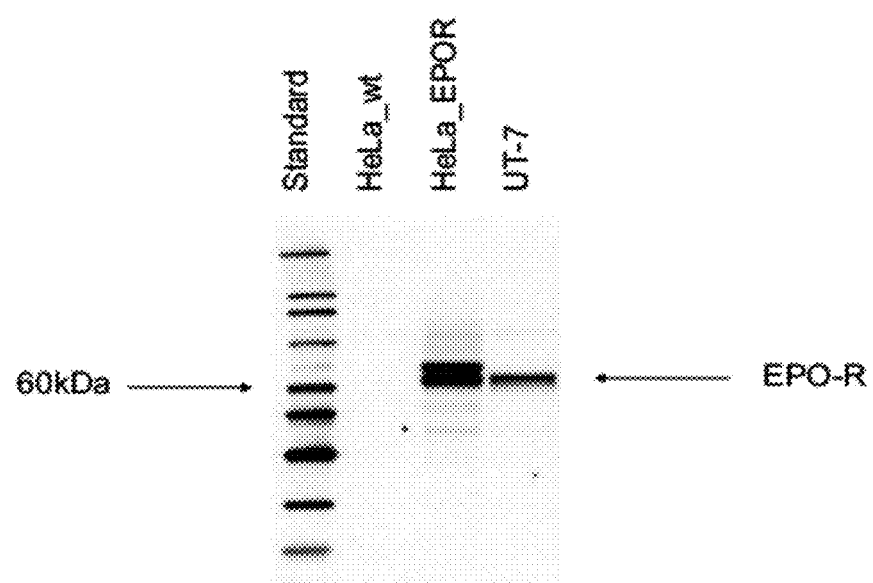
FIG. 1 Western Blot analysis of lysates from wt-HELA, HELA-EPOR and UT-7 cells.

SEQ ID NO: 01 Fragment of the human EPO receptor that has the amino acid sequence LPGPGGSVDIV.

SEQ ID NO: 02 Fragment of the human EPO receptor that has the amino acid sequence LDKWLLPRNPPSEDLPG-PGGSVDIV.

SEQ ID NO: 03 Amino acid sequence of the human EPO receptor precursor.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (likewise by Kd or KD or equilibrium constant). Affinity can be measured by common methods known in the art, including those described herein. When the affinity of polyclonal antibodies is determined, affinity is also denoted as "apparent affinity". Specific illustrative and exemplary embodiments for measuring binding affinity are described in the following.

The terms "anti-human EPO receptor antibody" and "an antibody that binds to human EPO receptor" refer to an antibody that is capable of binding human EPO receptor of SEQ ID NO: 03 with sufficient affinity such that the antibody is useful as a diagnostic and/or therapeutic agent in targeting human EPO receptor. In certain embodiments, an antibody that binds to human EPO receptor has a dissociation constant (Kd) of ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-human EPO receptor antibody binds to an epitope of human EPO receptor that is conserved among human EPO receptor from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia, C. and Lesk, A. M., J. Mol. Biol. 196 (1987) 901-917) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A. et al., Sequences of Proteins of Immunological Interest, 5th ed., Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extra-chromosomally or at a chromosomal location that is different from its natural chromosomal location.

"Isolated nucleic acid encoding an anti-human EPO receptor antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "obtainable from human endothelial cells" denotes in case of whole cells the process of paraformaldehyde fixation and in the case of tissue sections the process of deparaffinization followed by epitope retrieval in citrate buffer at 97° C. for 45 min.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "EPO receptor" refers to any native EPO receptor from any vertebrate source, including mammals such as primates (e.g. humans) and rodents (e.g., mice and rats), unless otherwise indicated. The term encompasses "full-length," unprocessed human EPO receptor as well as any form of human EPO receptor that results from processing in the cell. The term also encompasses naturally occurring variants of human EPO receptor, e.g., splice variants or allelic variants. The amino acid sequence of an exemplary human EPO receptor is shown in SEQ ID NO: 03.

The term "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al., Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the finding that antibodies which specifically bind to the human EPO receptor, especially to the human EPO receptor fragment of SEQ ID NO: 01, show no cross-reactivity or cross-binding to human epithelial or endothelial cells. In certain embodiments, antibodies that bind to human EPO receptor are provided. Antibodies of the invention are useful, e.g., for the diagnosis or treatment of anemia or cancer. Antibodies of the invention are also useful for the stratification of patients prior to the administration of a medicament that increases the number of red blood cells, especially prior to the administration of erythropoietin.

A. Exemplary Anti-Human EPO Receptor Antibodies

In one aspect, the invention provides isolated antibodies that bind to human EPO receptor. In certain embodiments, an anti-human EPO receptor antibody binds to human EPO receptor fragment LPGPGGSVDIV (EpoR (361-371); SEQ ID NO: 01).

| peptide | antibody | ka [1/Ms] | kd [1/sec] | $t/2_{diss}$ [min] | $K_A$ [1/M] | $K_D$ [nM] |
|---|---|---|---|---|---|---|
| EpoR (347-371) | GBb | $7.9*10^5$ | $5*10^{-4}$ | 23 | $1.6*10^9$ | 0.63 |
| EpoR (361-371) | GBb | $6.4*10^5$ | $1.1*10^{-3}$ | 10 | $5.7*10^8$ | 1.8 |

In one embodiment the herein provided antibody that binds to human EPO receptor binds to human EPO receptor fragment 361-371 with a comparable affinity (comparable Kd-values of the same magnitude) than to EPO receptor fragment 347-371.

In one embodiment the herein provided antibody that binds to human EPO receptor has an affinity ratio (Kd-value ratio) for binding to human EPO receptor fragment 361-371 to binding to human EPO receptor fragment 347-371 of less than 10, or less than 5, or about 3.

1. Antibody Affinity

In certain embodiments, an antibody provided herein has a dissociation constant (Kd) of ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, or e.g. from $10^{-9}$ M to $10^{-13}$ M).

In one embodiment, Kd is determined by a radiolabeled antigen binding assay (RIA) performed with the Fab version of an antibody of interest and its antigen as described by the following assay. Solution binding affinity of FABs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1° A polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd value is determined using surface plasmon resonance assays using a BIACORE®-2000 or a BIACORE®-3000 (BIAcore, Inc., Piscataway, N.J.) at 25° C. with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci.

USA 90 (1993) 6444-6448. Triabodies and tetrabodies are also described in Hudson, P. J. et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95). Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992)

581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for human EPO receptor and the other is for any other antigen. In certain embodiments, bispecific antibodies may bind to two different epitopes of human EPO receptor. Bispecific antibodies may also be used to localize cytotoxic agents to cells which express human EPO receptor. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting FAb" or "DAF" comprising an antigen binding site that binds to human EPO receptor as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

7. Antibody Variants a) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function (see, e.g., US 2003/0157108; US 2004/0093621). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2005/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech.

Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S, and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737, 056; WO 2004/056312, and Shields, R. L. et al., J. Biol. Chem. 276 (2001) 6591-6604)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

c) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Conjugation methods resulting in linkages which are substantially (or nearly) non-immunogenic are especially suited. Therefore, peptide- (i.e. amide-), sulfide-, (sterically hindered), disulfide-, hydrazone-, or ether linkage are especially suited. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and the antibody different conjugation strategies are at hand. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., Org. Biomol. Chem. 7 (2009) 3361-3371).

In general site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403).

Site specific reaction and covalent coupling can also be achieved by the selective reaction of terminal amino acids with appropriate modifying reagents.

The reactivity of an N-terminal cysteine with benzonitrils (see Ren, H. et al., Angew. Chem. Int. Ed. Engl. 48 (2009) 9658-9662) can be used to achieve a site-specific covalent coupling.

Native chemical ligation can also rely on C-terminal cysteine residues (Taylor, E. Vogel; Imperiali, B, Nucleic Acids and Molecular Biology (2009), 22 (Protein Engineering), 65-96).

EP 1 074 563 describes a conjugation method which is based on the faster reaction of a cysteine within a stretch of negatively charged amino acids with a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide the conjugate with 1:1 stoichiometry may be separated by chromatography from other conjugation side-products. This procedure can be facilitated by using a dye labeled binding pair member and a charged linker. By using this kind of labeled and highly negatively charged binding pair member, mono conjugated polypeptides are easily separated from non labeled polypeptides and polypeptides which carry more than one linker, since the difference in charge and molecular weight can be used for separation. The fluorescent dye can be useful for purifying the complex from un-bound components, like a labeled monovalent binder.

In one embodiment the effector moiety is selected from the group consisting of a binding moiety, a labeling moiety, and a biologically active moiety.

B. Recombinant Methods and Compositions

Antibodies may be produced using recombinant methods and compositions, e.g., as described in U.S. Pat. No. 4,816,567. In one embodiment, isolated nucleic acid encoding an anti-human EPO receptor antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-human EPO receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human EPO receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, N.J. (2003), pp. 245-254, describing expression of antibody fragments in E. coli). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see Gerngross, T. U., Nat. Biotech. 22 (2004) 1409-1414; and Li, H. et al., Nat. Biotech. 24 (2006) 210-215).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-human EPO receptor antibodies provided herein may be identified, screened for, or characterized for their physical/chemical properties and/or biological activities by various assays known in the art.

1. Immunohistochemical Staining Assays

In one aspect, tissue sections are deparaffinized, i.e. the paraffin is removed, followed by epitope retrieval using e.g. a citrate buffer (as available from Vector Laboratories) for treatment at elevated temperatures, such as for a treatment for 45 min at 97° C. After blocking (e.g. with Protein Block Serum-Free (cat no. X0909, available from DAKO Deutschland GmbH)), tissue sections are incubated with the primary antibody, e.g. in case of the antibody as reported herein at a concentration of 127.5 ng/ml for 60 min. Afterwards the bound antibody is determined, e.g. with the Envision polyclonal rabbit detection kit (DAKO Deutschland GmbH). Finally, specimens are counterstained, dehydrated and mounted.

2. Stratification of Patients by Determining the EPO Receptor Status of Cancer Cells Sample material from patients is collected either from tissue material from a tumor resection, e.g. performed to treat the cancer disease, or by tumor biopsy. Collected tumor tissue is fixed with formalin and embedded in paraffin according to histological standard procedures. Immunohistochemistry using the anti-EPO receptor antibody as reported herein is performed on sections of this tumor material (see above and examples). Histopathological assessment of stained tissue sections allows for the determination whether the tumor tissue is EPO receptor positive or negative. This assessment can be based on a scoring system which takes into account the intensity of the staining of tumor cells and the number of stained tumor cell in a defined section area.

Assessment of EPO receptor status of the tumor tissue of a patient can be the basis for determining an optimized treatment of the cancer patient. This includes prognosis of tumor progression, intensity of anti-tumor therapies like radiation therapy, chemotherapy, therapy by specific anti-tumor agents, treatment of chemotherapy or tumor disease-associated anemia, change in dose or administration schedule of an erythropoiesis stimulating agent (ESA) used to correct the anemic condition of the patient, discontinuation of the anti-anemic treatment with an ESA, change from one particular type of ESA to another type of ESA, switch from anti-anemia treatment with an ESA to transfusions of blood or separated and concentrated erythrocytes (packed red blood cells), or a decision to postpone or to refrain from future treatments with an ESA.

ESAs are agents which stimulate erythropoiesis e.g. by stimulation of the erythropoietin receptor like recombinant human erythropoietins, or epoetins, modified erythropoietins, continuous erythropoietin receptor stimulators, small molecule or peptidic erythropoietin receptor agonists, stabilizers of hypoxia inducible factors etc.

D. Methods and Compositions for Diagnostics and Detection

In certain embodiments, any of the anti-human EPO receptor antibodies provided herein is useful for detecting the presence of human EPO receptor in a biological sample. The term "detecting" as used herein encompasses quantitative or qualitative detection. In certain embodiments, a biological sample comprises a cell or tissue, such as PBMCs (peripheral blood monocytic cells), tissue sections or samples from normal or diseased tissues, fresh tissues, frozen tissues, formalin-fixed, paraffin-embedded (FFPE) tissues.

In one embodiment, an anti-human EPO receptor antibody for use in a method of diagnosis or detection is provided. In a further aspect, a method of detecting the presence of human EPO receptor in a biological sample is provided. In certain embodiments, the method comprises contacting the biological sample with an anti-human EPO receptor antibody as described herein under conditions permissive for binding of the anti-human EPO receptor antibody to human EPO receptor, and detecting whether a complex is formed between the anti-human EPO receptor antibody and human EPO receptor. Such method may be an in vitro or in vivo method. In one embodiment, an anti-human EPO receptor antibody is used to select subjects eligible for therapy with a recombinant human EPO (epoetin), hyperglycosylated human erythropoietins, erythropoietin receptor agonists, erythropoietin mimetic peptides, chemical erythropoietin receptor activating compounds or other erythropoiesis stimulating agents (ESAs) e.g. where human EPO receptor is a biomarker for selection and/or stratification of patients, or adjusting the dose used in such therapies.

Exemplary disorders that may be diagnosed using an antibody of the invention include e.g. cancer or also EPOR status of stem cells—for tissue regeneration.

In certain embodiments, labeled anti-human EPO receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-human EPO receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinyl pyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the anti-human EPO receptor antibodies provided herein may be used in therapeutic methods.

In a further aspect, the invention provides for the use of an anti-human EPO receptor antibody in the manufacture or preparation of a medicament.

In a further aspect, the invention provides pharmaceutical formulations comprising any of the anti-human EPO receptor antibodies provided herein. In one embodiment, a pharmaceutical formulation comprises any of the anti-human EPO receptor antibodies provided herein and a pharmaceutically acceptable carrier. In another embodiment, a pharmaceutical formulation comprises any of the anti-human EPO receptor antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-human EPO receptor antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-human EPO receptor antibody.

IV. Examples

The following are examples of methods and compositions of the invention. It is understood that various other embodiments may be practiced, given the general description provided above.

Example 1

Generation of Antibodies Directed Against the Intracellular Domain of the Human EPOR A 25 amino-acid synthetic peptide corresponding to residues 347-371 of the mature human erythropoietin receptor (LDKWLLPRNPPSEDLPGPGGSVDIV, SEQ ID NO: 02) was used as immunogen (corresponds to amino acid residues 371-395 of the EPO receptor precursor, SEQ ID NO: 03).

For immunization, peptides were coupled to KLH (keyhole limpet haemocyanine) via a C-terminal cysteine residue. Rabbits were immunized with the protein every 4 weeks for 3-5 times. First level screening for specific antibodies was done by testing on ELISA microtiter plates coated either with protein or biotinylated peptides according to established procedures.

Polyclonal sera were precipitated by ammonium sulphate. IgGs were separated by DEAE chromatography and further purified by immunoaffinity adsorption on a peptide presenting column containing amino acid residues 361-371 of the mature hEPO receptor (SEQ ID NO: 01). IgGs were recovered from the column using propionic acid, pH 2.6. The obtained solution was adjusted to pH 7.3 using TRIS buffer (2.5 M, pH 8.5). Next, purified IgGs were dialyzed against 50 mM potassium phosphate/150 mM KCl buffer followed by gel filtration on a Superdex 200 column (GE Healthcare) using the same buffer and finally sterile filtered using a 0.2 µm membrane filter.

Example 2

Generation of EPO Receptor Expressing HELA Cells

For generating stably transfected HELA cells expressing recombinant human EPO receptor (EPOR), cells were transduced with the supernatant from HEK 293 cells transiently transfected with a retroviral expression vector encoding EPO receptor or EPO receptor-eGFP (as fusion protein to the intracellular C-terminus, Invitrogen) and pVSV-G (an expression vector encoding the G glycoprotein of the rhabdovirus vesicular stomatitis virus). Two days after transduction the medium was replaced with fresh supplemented RPMI containing 0.2 mg/ml zeocin.

For transient transfection experiments $8 \times 10^4$ HELA cells were plated on cover slips in a 12-well plate in 1 ml medium using FuGENE Transfection reagent (Roche Molecular Biochemicals Cat. No. 1815075). In detail, 3 µl of FuGENE 6 were added to 97 µl RPMI 1640 without FCS, incubated for 5 min at RT. Thereafter, 1 µg DNA mix was added and incubated for 15 min at RT. Finally, 50 µl of the DNA/FuGENE 6 solution was added to 1 ml cell culture medium containing the cells on cover slips.

Example 3

Generation of EPO Receptor Expressing UT7 Cells

UT-7 cell line is a human factor-dependent erythroleukemic cell line (Human bone marrow acute myeloid leukemia cell line DSMZ: ACC 137), requiring EPO for long-term growth. UT7 cells were maintained in RPMI medium supplemented with L-glutamine (2 mM), non-essential amino acids (1×), sodium pyruvate (1 mM), 10% fetal calf serum and 10 U/ml GM-CSF. Transduced cells (UT7/EPOR) were maintained in the same medium as non-transduced cells with 25 U/ml GM-CSF instead of 10 U/ml with the addition of 0.4 mg/ml zeocin. Before each stimulation the cells were starved by incubation overnight in RPMI media supplemented with L-glutamine (2 mM), non-essential amino acids (1×), sodium pyruvate (1 mM) and 0.1% fetal calf serum.

UT-7 cells were transduced with the supernatant from HEK 293 cells transiently transfected with a retroviral expression vector encoding EPO receptor and pVSV-G. Two days after transduction the medium was replaced with fresh supplemented RPMI containing 0.4 mg/ml zeocin and 25 U/ml GM-CSF. After selection a cell line of UT-7 cells stable expressing EPO receptor on their surface was obtained.

Example 4

SDS-PAGE and Western Blotting

The SDS-PAGE and western blotting were performed according to standard procedures and the NuPAGE gel system of Invitrogen. The extracts corresponding to different number of cells were loaded in each line of a NuPAGE Novex 4-12% Bis-Tris gel. After gel electrophoresis the proteins were transferred onto PVDF membranes and incubated with an anti-EPO receptor antibody obtained in example 1 overnight at 4° C. After washing, the membranes were incubated with a conjugate anti-mouse or anti-rabbit IgG-HRP and developed using ECL reagents (LUMI-Light® PLUS western blotting substrate, Roche Diagnostics GmbH, Mannheim, Germany). Results are shown in FIG. 1.

Example 5

BIACORE Analysis

Kinetics of anti-EPO receptor antibody GBb binding to the EPO receptor fragments was determined at 25° C.

Antibody GBb displays nanomolar avidity to the EPO receptor fragment 361-371 and nanomolar avidity to EPO receptor fragment 347-371. The antibody shows a long dissociation constant (t/2 diss).

The antibody GBb was captured to the flow cell of the sensor chip using goat anti-rabbit Fcγ antibody followed by perfusion with EPO receptor fragment 347-371 or 361-371, respectively.

Measurements were made on a BIACORE® 3000 instrument at 25° C. in HBS-EP-Buffer, pH 7.4 (10 mM HEPES, 150 mM NaCl, 3.4 mM EDTA, 0.005% polysorbate 20 (w/v)). 1.0 mg/ml CMD (carboxymethyldextrane) was added to reduce unspecific binding. The GBb antibody displays nanomolar binding avidity to the corresponding EPO receptor fragment of SEQ ID NO: 01.

Example 6

Immunocytochemistry I

Immunocytochemistry analysis of affinity purified polyclonal antibody directed against EPO receptor on transiently transfected HELA EPOR cells were performed as follows: HELA cells cultured on glass coverslips were transfected to transiently express EPO receptor-GFP fusion protein, PFA (paraformaldehyde) fixed, and stained with 1.0-10 µg/ml purified IgG of a polyclonal antibody binding to EPO receptor. Bound antibodies were detected by CY3 goat anti-human IgG secondary antibodies. Specimens were imaged on a LEICA confocal laser scanning microscope SP2 using 488 nm and 543 nm excitation for Alexa Fluor 488 and CY3 respectively.

Anti-EPO receptor antibody immunoreactivity was found to be closely co-localized with the green fluorescence of the EPO receptor-GFP fusion protein. The antibody also recognizes newly synthesized EPO receptor that is confined to the ER/Golgi region. The lack of any detectable labeling in non-transfected cells also confirms the high specificity of the anti-EPO receptor polyclonal antibodies as reported herein.

Figure 2:
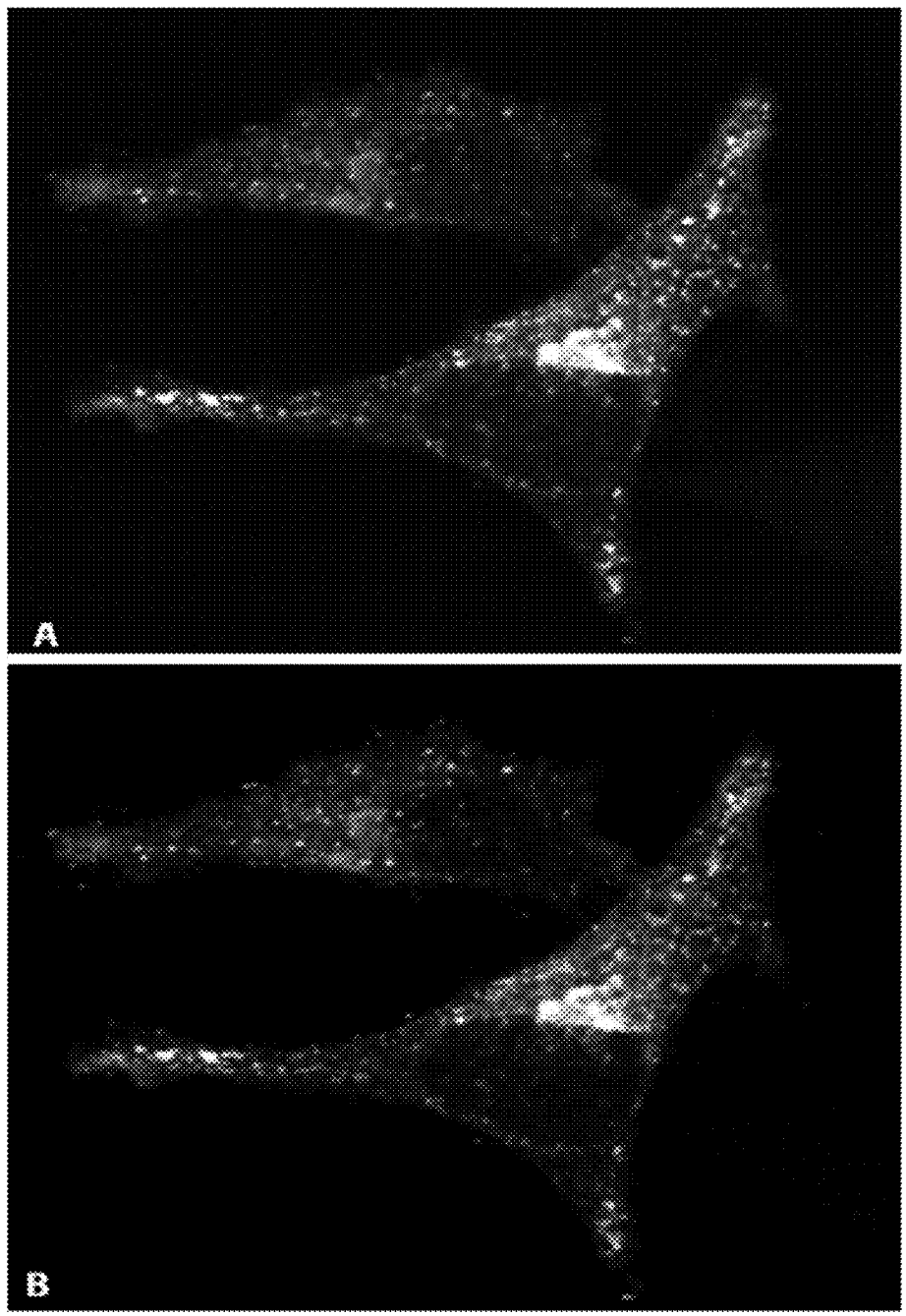
FIGS. 2A-B Immunocytochemical analysis of wt-HELA and HELA-EPOR cells: A: EPO receptor-GFP fusion protein; B: exemplary antibody as reported herein.

Results are shown in FIG. 2.

Example 7

Immunohistochemistry II

Figure 3:
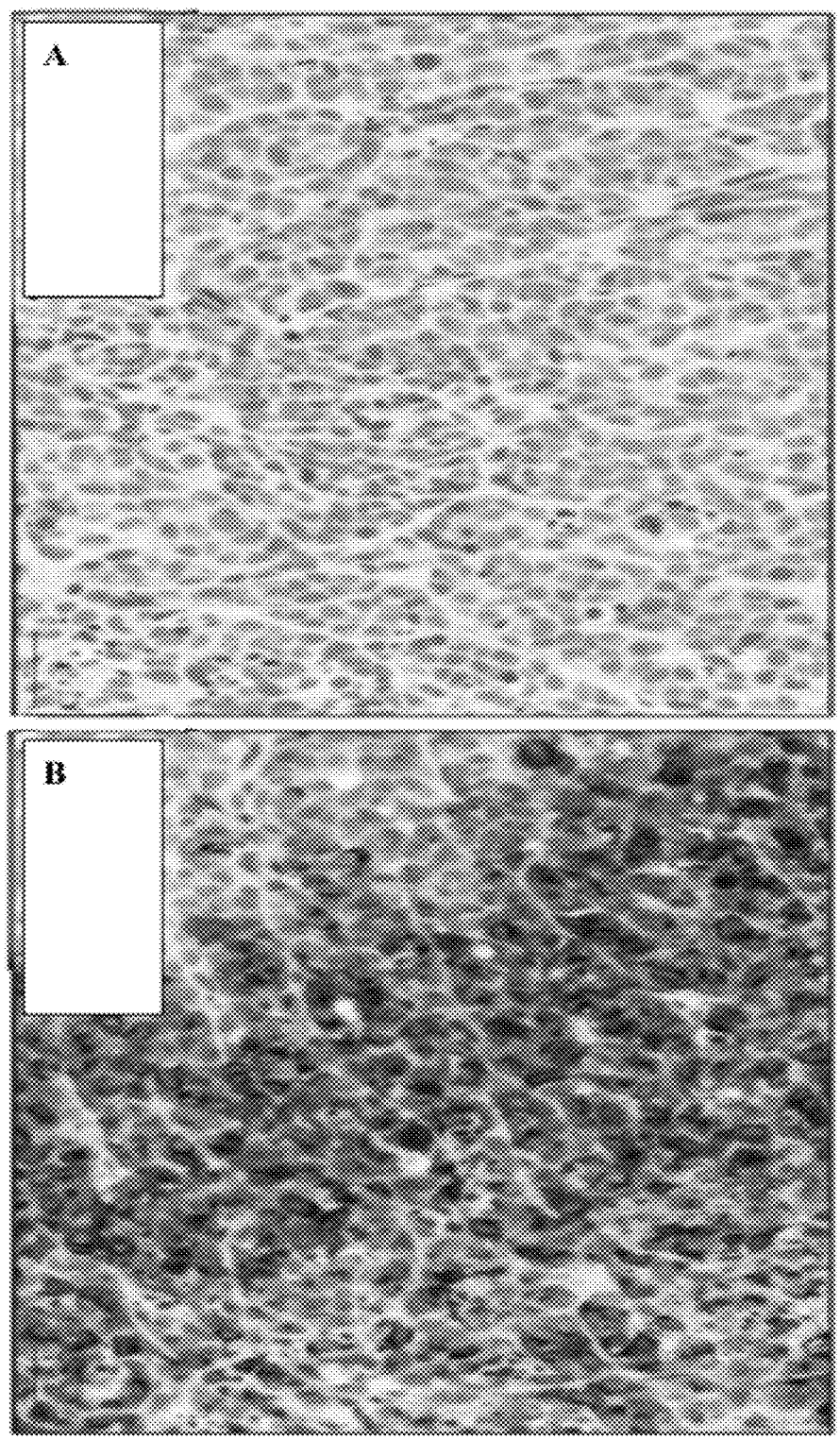
FIGS. 3A-B Immunohistochemical analysis of wt-HELA and HELA-EPOR cells: A: wild-type HELA cells; B: EPOR-HELA.

Tissue sections of xenograft tissue from either HELA EPOR or wt-HELA cells (neg. for EPOR expression) were deparaffinized followed by epitope retrieval in citrate buffer (Vector Laboratories) at 97° C. for 45 min. Automated staining was performed on a Labvision instrument. The anti-EPO receptor antibody was used at 127.5 ng/ml final concentration. The primary antibody was detected using the Envision Polyclonal Rabbit detection kit (DAKO Deutschland GmbH). Images were taken on a Zeiss Axiovision Rel 4.8, Microscope (see FIG. 3).

| peptide | antibody | ka [1/Ms] | kd [1/sec] | t/2diss [min] | KA [1/M] | KD [nM] | Chi² RU² |
|---|---|---|---|---|---|---|---|
| EPOR (347-371) | GBb | 7.9E+05 | 5.0E−04 | 23 | 1.6E+09 | 0.63 | 0.3 |
| EpoR (361-371) | GBb | 6.4E+05 | 1.1E−03 | 10 | 5.7E+08 | 1.8 | 0.1 |

Example 8

Western Blot Analysis on UT-7 Cells, Human Umbilical Vein (HUVEC) and Human Microvascular Endothelial (HMVEC) Cells Methods as described in Example 4 were used.

Figure 4:
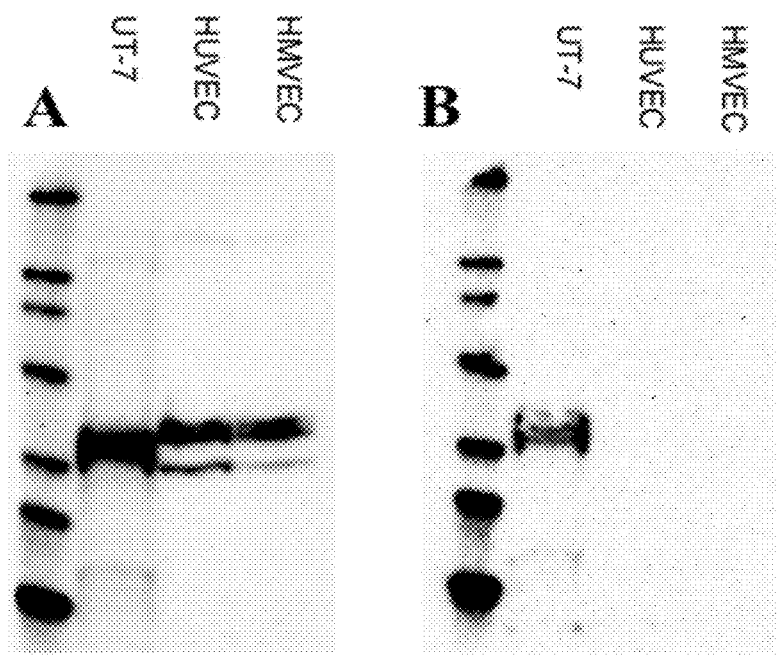
FIGS. 4A-B Western Blot analysis of lysates from UT-7, HUVEC (human umbilical vein endothelial cells) and HMVEC cells (human microvascular endothelial cells).

Panel A in FIG. 4 shows the immunoreactivity of an antibody binding to the EPO receptor fragment LDKWLLPRN-PPSEDLPGPGGSVDIV (SEQ ID NO: 02).

Panel B in FIG. 4 shows the immunoreactivity of an antibody cross-adsorbed to the EPO receptor fragment LPG-PGGSVDIV (SEQ ID NO: 01).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for detecting human erythropoietin (EPO) receptor in vitro comprising
    determining in vitro the presence of human EPO receptor in a sample by incubating the sample with an EPO receptor antibody that specifically binds to human EPO receptor fragment of SEQ ID NO: 01 thereby detecting in vitro human EPO receptor,
    wherein the EPO receptor antibody that specifically binds to EPO receptor fragment of SEQ ID NO: 01 does not specifically bind to a protein obtainable from human endothelial cells that has a molecular weight of about 66 kD.

2. The method according to claim 1, wherein the antibody does not specifically bind to a protein obtainable from human endothelial cells that has a molecular weight of about 58 kD to about 70 kD.

3. The method according to claim 1, wherein the antibody binds to a protein obtainable from human endothelial cells with an affinity of $10^{-3}$M or higher.

4. The method according to claim 1, wherein the antibody is a polyclonal antibody or a monoclonal antibody.

5. The method according to claim 1, wherein the antibody is a human, humanized, or chimeric antibody.

6. The method according to claim 1, wherein the antibody is an antibody fragment that binds human EPO receptor.

7. The method of claim 1, wherein the sample is a human tissue or cell sample.

8. The method according to claim 7, wherein the sample is a lysate of human tissue or cells, or a section of human tissue, or a section of a fresh human tissue, or frozen human tissue, or a section of frozen human tissue, or formalin-fixed paraffin embedded human tissue, or a section of formalin-fixed paraffin embedded human tissue.

9. The method according to claim 7, wherein analysis is performed by immunochemistry, immunofluorescence or immunohistochemistry.

10. The method according to claim 7, wherein analysis is performed by Western Blot.

\* \* \* \* \*